United States Patent [19]

Feitelson et al.

[11] Patent Number: 5,667,993
[45] Date of Patent: Sep. 16, 1997

[54] **PRIMERS AND PROBES FOR THE IDENTIFICATION OF *BACILLUS THURINGIENSIS* GENES AND ISOLATES**

[75] Inventors: Jerald S. Feitelson; Kenneth E. Narva, both of San Diego, Calif.

[73] Assignee: Mycogen Corporation, San Diego, Calif.

[21] Appl. No.: 540,104

[22] Filed: Oct. 6, 1995

[51] Int. Cl.$^6$ ............................ C12P 19/34; C12Q 1/68; C07H 21/04; C12N 15/00
[52] U.S. Cl. ...................... 435/91.2; 435/6; 435/183; 435/832; 536/23.7; 536/24.32; 536/24.33; 536/23.71; 935/8; 935/77; 935/78
[58] Field of Search .......................... 435/6, 183, 91.2, 435/91.1, 252.31, 832; 536/23.7, 24.32, 24.33, 23.71; 935/8, 72, 78

[56] References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 435/328.1 |
| 4,797,276 | 1/1989 | Hernstadt et al. | 424/84 |
| 4,853,331 | 8/1989 | Hernstadt et al. | 435/252.3 |
| 4,918,006 | 4/1990 | Ellar et al. | 435/69.1 |
| 4,948,734 | 8/1990 | Edwards et al. | 514/2 |
| 4,990,332 | 2/1991 | Payne et al. | 424/93.461 |
| 5,039,523 | 8/1991 | Payne et al. | 424/93.461 |
| 5,093,120 | 3/1992 | Edwards et al. | 514/2 |
| 5,126,133 | 6/1992 | Payne et al. | 424/93.461 |
| 5,151,363 | 9/1992 | Payne | 435/252.5 |
| 5,164,180 | 11/1992 | Payne et al. | 424/93.461 |
| 5,169,629 | 12/1992 | Payne et al. | 424/93.461 |
| 5,204,237 | 4/1993 | Gaertner et al. | 435/6 |
| 5,236,843 | 8/1993 | Narva et al. | 435/252.3 |
| 5,262,399 | 11/1993 | Hickle et al. | 424/93.2 |
| 5,270,448 | 12/1993 | Payne | 514/2 |
| 5,281,530 | 1/1994 | Sick et al. | 435/252.3 |
| 5,322,932 | 6/1994 | Narva et al. | 530/350 |
| 5,350,577 | 9/1994 | Payne | 424/93.461 |
| 5,426,049 | 6/1995 | Sick et al. | 435/252.3 |
| 5,439,881 | 8/1995 | Narva et al. | 514/2 |

OTHER PUBLICATIONS

Metcalf, R.L. (1986) "Methods for the Study of Pest Diabrotica", pp. xii–xv.

Schnepf, H.E., H.R. Whiteley (1981) "Cloning and expression of the *Bacillus thuringiensis* crystal protein gene in *Escherichia coli*", Proc. Natl. Acad. Sci. USA 78(5):2893–2897.

Feitelson, J.S. et al. (1992) "*Bacillus thuringiensis:* Insects and Beyond" Bio/Technology 10:271–275.

Hofte, H., H.R. Whiteley (1989) "Insecticidal Crystal Proteins of *Bacillus thuringiensis*", Microbiological Reviews 53(2):242–255.

Kreig, V.A. et al. (1983) "*Bacillus thuringiensis* var. *tenebrionis:* ein neuer, gegenuber Larven von Colepteren wirksamer Pathotyp" Z. ang. Ent. 96:500–508

Beegle, C.C. (1978) "Use of Entomogenous Bacteria in Agroecosystems" Developments in Industrial Microbiology 20:97–104.

Couch, T.L. (1980) "Mosquito Pathogenicity of *Bacillus thuringiensis* var. *israelensis*" Developments in Industrial Microbiology 22:61–67.

Gaertner, F. (1990) "Cellular delivery systems for insecticidal proteins: living and non–living microorganisms" Controlled Delivery of Crop–Protection Agents, pp. 245–257.

Gaertner, F., L. Kim (1988) "Current Applied Recombinant DNA Projects" TIBTECH 6:S4–S7.

Bottjer, K.P. et al. (1985) "Nematoda: Susceptibility of the Egg to *Bacillus thuringiensis* Toxins" Experimental Parasitology 60:239–244.

Ignoffo, C.M., V.H. Dropkin (1977) "Deleterious Effects of the Thermostable Toxin of *Bacillus thuringiensis* on Species of Soil–Inhabiting, Myceliophagus, and Plant–Parasitic Nematodes" Journal of the Kansas Entomological Society 50(3):394–398.

Ciordia, H. W.E. Bizzell (1961) "A Preliminary Report on the Effects of *Bacillus thuringiensis* var. *thuringiensis* Berliner on the Development of the Free–Living Stages of Some Cattle Nematodes" Journal of Parasitology 47:41, *abstract No. 86.

Coles, G.C. (1986) "Anthelmintic Resistance in Sheep" Veterinary Clinics of North American, Food Animal Practice 2(2):423–432.

Prichard, R.K. et al. (1980) "The Problem of Anthelmintic Resistance in Nematodes" Australian Veterinary Journal 56:239–251.

Carozzi, N.B. et al. (1991) "Prediction of Insecticidal Activity of *Bacillus thuringiensis* Strains by Polymerase Chain Reaction Product Profiles" Applied and Environmental Microbiology 57(11):3057–3061.

*Primary Examiner*—Bradley L. Sisson
*Attorney, Agent, or Firm*—Saliwanchik, Lloyd & Saliwanchik

[57] ABSTRACT

Disclosed and claimed are novel nucleotide primers for the identification of genes encoding toxins active against nematodes and coleopterans. The primers are useful in PCR techniques to produce gene fragments which are characteristic of genes encoding these toxins. The primers are also useful as nucleotide probes to detect the toxin-encoding genes.

2 Claims, No Drawings

PRIMERS AND PROBES FOR THE IDENTIFICATION OF *BACILLUS THURINGIENSIS* GENES AND ISOLATES

Background of the Invention

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering these *B.t.* endotoxins to agricultural environments are under development, including the use of plants genetically engineered with endotoxin genes for insect resistance and the use of stabilized intact microbial cells as *B.t.* endotoxin delivery vehicles (Gaertner, F. H., L. Kim [1988] *TIBTECH* 6:S4–S7). Thus, isolated *B.t.* endotoxin genes are becoming commercially valuable.

Until the last ten years, commercial use of *B.t.* pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

In recent years, however, investigators have discovered *B.t.* pesticides with specificities for a much broader range of pests. For example, other species of *B.t.*, namely *israelensis* and *morrisoni* (a.k.a. *tenebrionis*, a.k.a. *B.t.* M-7, a.k.a. *B.t. san diego*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. *israelensis*," *Developments in Industrial Microbiology* 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508, describe *Bacillus thuringiensis* var. *tenebrionis*, which is reportedly active against two beetles in the order Coleoptera. These are the Colorado potato beetle, *Leptinotarsa decemlineata*, and *Agelastica alni*.

Recently, new subspecies of *B.t.* have been identified, and genes responsible for active δ-endotoxin proteins have been isolated (Höfte, H., H. R. Whiteley [1989] *Microbiological Reviews* 52(2):242–255). Höfte and Whiteley classified *B.t.* crystal protein genes into four major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271–275). CryV has been proposed to designate a class of toxin genes that are nematode-specific.

The cloning and expression of a *B.t.* crystal protein gene in *Escherichia coli* has been described in the published literature (Schnepf, H. E., H. R. Whiteley [1981] *Proc. Natl. Acad. Sci. USA* 78:2893–2897). U.S. Pat. No. 4,448,885 and U.S. Pat. No. 4,467,036 both disclose the expression of *B.t.* crystal protein in *E. coli*. U.S. Pat. Nos. 4,990,332; 5,039,523; 5,126,133; 5,164,180; and 5,169,629 are among those which disclose *B.t.* toxins having activity against lepidopterans. U.S. Pat. Nos. 4,797,276 and 4,853,331 disclose *B. thuringiensis* strain *tenebrionis* which can be used to control coleopteran pests in various environments. U.S. Pat. No. 4,918,006 discloses *B.t.* toxins having activity against dipterans. U.S. Pat. No. 5,151,363 and U.S. Pat. No. 4,948,734 disclose certain isolates of *B.t.* which have activity against nematodes. Other U.S. Patents which disclose activity against nematodes include 5,093,120; 5,236,843; 5,262,399; 5,270,448; 5,281,530; 5,322,932; 5,350,577; 5,426,049; and 5,439,881. As a result of extensive research and investment of resources, other patents have issued for new *B.t.* isolates and new uses of *B.t.* isolates. See Feitelson, J. S., J. Payne, L. Kim (1992) *Bio/Technology* 10:271–275 for a review. However, the discovery of new *B.t.* isolates and new uses of known *B.t.* isolates remains an empirical, unpredictable art.

Regular use of chemical control of unwanted organisms can select for chemical resistant strains. Chemical resistance occurs in many species of economically important insects and has also occurred in nematodes of sheep, goats, and horses. The development of chemical resistance necessitates a continuing search for new control agents having different modes of action. The subject invention pertains specifically to materials and methods for the identification of *B.t.* toxins active against nematodes or coleopteran pests. Of particular interest among the coleopteran pests is the corn rootworm.

In recent times, the accepted methodology for control of nematodes has centered around the drug benzimidazole and its congeners. The use of these drugs on a wide scale has led to many instances of resistance among nematode populations (Prichard, R. K. et al. [1980] "The problem of anthelmintic resistance in nematodes," *Austr. Vet. J.* 56:239–251; Coles, G. C. [1986] "Anthelmintic resistance in sheep," In *Veterinary Clinics of North America: Food Animal Practice*, Vol 2:423–432 [Herd, R. P., Eds.] W. B. Saunders, New York). There are more than 100,000 described species of nematodes.

A small number of research articles have been published about the effects of delta endotoxins from *B. thuringiensis* species on the viability of nematode eggs. Bottjer, Bone and Gill ([1985] *Experimental Parasitology* 60:239–244) have reported that *B.t. kurstaki* and *B.t. israelensis* were toxic in vitro to eggs of the nematode *Trichostrongylus colubriformis*. In addition, 28 other *B.t.* strains were tested with widely variable toxicities. Ignoffo and Dropkin (Ignoffo, C. M., Dropkin, V. H. [1977] *J. Kans. Entomol. Soc.* 50:394–398) have reported that the thermostable toxin from *Bacillus thuringiensis* (beta exotoxin) was active against a free-living nematode, *Panagrellus redivivus* (Goodey); a plant-parasitic nematode, *Meloidogyne incognita* (Chitwood); and a fungus-feeding nematode, *Aphelenchus avena* (Bastien). Beta exotoxin is a generalized cytotoxic agent with little or no specificity. Also, H. Ciordia and W. E. Bizzell ([1961] *Jour. of Parasitology* 47:41 [abstract]) gave a preliminary report on the effects of *B. thuringiensis* on some cattle nematodes.

There are a number of beetles that cause economic damage. For example, Chrysomelid beetles such as flea beetles and corn rootworms and curculionids such as alfalfa weevils are particularly important pests. Flea beetles include a large number of small leaf feeding beetles that feed on the leaves of a number of grasses, cereals and herbs. Flea beetles include a large number of genera (e.g., Altica, Apphthona, Argopistes, Disonycha, Epitrix, Longitarsus, Prodagricomela, Systena, and Phyllotreta). The flea beetle, *Phyllotreta cruciferae*, also known as the rape flea beetle, is a particularly important pest. Corn rootworms include species found in the genus Diabrotica (e.g., *D. undecimpunctata undecimpunctata*, *D. undecimpunctata howardii*, *D. longicornis*, *D. virgifera* and *D. balteata*). Corn rootworms cause extensive damage to corn and curcubits. The western spotted cucumber beetle, *D. undecimpunctata undecimpunctata*, is a pest of curcubits in the western U.S. Alfalfa weevils (also known as clover weevils) belong to the genus, Hypera (*H. postica*, *H. brunneipennis*, *H. nigrirostris*, *H. punctata* and *H. meles*), and are considered an important pest of legumes. The Egyptian alfalfa weevil, *H. brunneipennis*, is an important pest of alfalfa in the western U.S.

Approximately $250 million worth of insecticides are applied annually to control corn rootworms alone in the United States. In the Midwest, $60 million and $40 million worth of insecticide were applied in Iowa and Nebraska, respectively, in 1990. It has been estimated that the annual cost of insecticides to control corn rootworm and the annual crop losses caused by corn rootworm damage exceeds a total of $1 billion in the United States each year (Meycalf, R. L. [1986] in *Methods for the Study of Pest Diabrotica*, Drysan, J. L. and T. A. Miller [Eds.], Springer-Verlag, New York, N.Y., pp. vii–xv). The corn rootworm (Diabrotica spp.) is a coleopteran pest which causes extensive damage to corn crops each year due to root feeding by the larvae. Three main species of corn rootworm, Western corn rootworm (*Diabrotica virgifera virgifera*), Northern corn rootworm (*Diabrotica barberi*), and Southern corn rootworm (*Diabrotica undecimpunctata howardi*) cause varying degrees of damage to corn in the United States. Even with insecticide use, rootworms cause about $750 million worth of crop damage each year, making them the most serious corn insect pest in the Midwest.

The life cycle of each Diabrotica species is similar. The eggs of the corn rootworm are deposited in the soft. Newly hatched larvae (the first instar) remain in the ground and feed on the smaller branching corn roots. Later instars of Western and Northern corn rootworms invade the inner root tissues that transport water and mineral elements to the plants. In most instances, larvae migrate to feed on the newest root growth. Tunneling into roots by the larvae results in damage which can be observed as brown, elongated scars on the root surface, tunneling within the roots, or varying degrees of pruning. Plants with pruned roots usually dislodge after storms that are accompanied by heavy rains and high winds. The larvae of Southern corn rootworm feed on the roots in a similar manner as the Western and Northern corn rootworm larvae. Southern corn rootworm larvae may also feed on the growing point of the stalk while it is still near the soil line, which may cause the plant to wilt and die.

After feeding for about 3 weeks, the corn rootworm larvae leave the roots and pupate in the soft. The adult beetles emerge from the soft and may feed on corn pollen and many other types of pollen, as well as on corn silks. Feeding on green silks can reduce pollination level, resulting in poor grain set and poor yield. The Western corn rootworm adult also feeds upon corn leaves, which can slow plant growth and, on rare occasions, kill plants of some corn varieties.

Current methods for controlling corn rootworm damage in corn are limited to the use of crop rotation and insecticide application. However, economic demands on the utilization of farmland restrict the use of crop rotation. In addition, an emerging two-year diapause (or overwintering) trait of Northern corn rootworms is disrupting crop rotations in some areas.

The use of insecticides to control corn rootworm and other coleopteran pests also has several drawbacks. Continual use of insecticides has allowed resistant insects to evolve. Extremely high populations of larvae, heavy rains, and improper calibration of insecticide application equipment can result in poor control. Insecticide use often raises environmental concerns such as contamination of soil and of both surface and underground water supplies. Working with insecticides may also pose hazards to the persons applying them.

At the present time there is a need to have more effective means to control the many nematodes and the corn rootworm that cause considerable damage to susceptible hosts and crops. Advantageously, such effective means would employ specific biological agents.

*Bacillus thuringiensis* toxins which are active against nematodes and corn rootworm are now known. However, to date, the method for isolating the responsible toxin genes has been a slow empirical process. That is, for a given active *B.t.* isolate, there is currently no rapid systematic method for identifying the responsible toxin genes or for predicting the activity of a given *B.t.* isolate. The subject invention helps to eliminate the empirical nature of finding certain *B.t.* insecticidal protein toxin genes. Although the process is still highly unpredictable, this invention facilitates expedient identification of potentially new commercially valuable insecticidal isolates and endotoxin genes.

A recent report of similar methods has appeared (see Carozzi, N. B., V. C. Kramer, G. W. Warren, S. Evola, G. Koziel [1991] *Appl. Env. Microbiol.* 57(11):3057–3061). This report does not disclose or suggest the specific primers and probes of the subject invention for nematode-active and corn rootworm-active toxin genes. U.S. Pat. No. 5,204,237 describes specific and universal probes for the isolation of *B.t.* toxin genes. This patent, however, does not describe the probes and primers of the subject invention.

BRIEF SUMMARY OF THE INVENTION

The subject invention concerns unique nucleotide sequences which are useful primers in PCR techniques. The primers produce gene fragments which are characteristic of genes encoding nematode- or coleopteran-active toxins and, thus, can be used in the identification and isolation of specific toxin genes.

In specific embodiments, the invention concerns the following sequence segments:

1. A forward primer designated V3 whose nucleotide sequence is GATCGTMTWGARTTTRTTCC (SEQ ID NO. 1);

2. A forward primer designated V5 whose nucleotide sequence is AAAGTNGATGCMTTATCWGATGA (SEQ ID NO. 2);

3. A forward primer designated V7 whose nucleotide sequence is ACACGTATAHDGTTTCTGG (SEQ ID NO. 3);

4. A reverse primer designated ΔV5' whose nucleotide sequence is TCATCWGATAAKGCATCNAC (SEQ ID NO. 4); and 5. A reverse primer designated ΔV8' whose nucleotide sequence is TGGACGDTCTTCAMKAATTTCYAAA (SEQ ID NO. 5).

In one embodiment of the subject invention, *B.t.* isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of toxin-encoding genes will be amplified by the procedure, thus identifying the presence of the gene.

Another important aspect of the subject invention is the use of the nucleotide sequences disclosed as probes to detect genes encoding *B.t.* toxins which are active against nematodes or coleopterans. The probes are particularly useful for the identification of genes which encode toxins active against corn rootworm. The probes may be RNA or DNA. The probe will normally have at least about 10 bases, more usually at least about 18 bases, and may have up to about 50 bases or more, usually not having more than about 200 bases if the probe is made synthetically. However, longer probes can readily be utilized, and such probes can be, for example, several kilobases in length. The probe sequence is designed to be at least substantially complementary to a gene encoding a toxin of interest. The probe need not have perfect complementarity to the sequence to which it hybridizes. The probes may be labelled utilizing techniques which are well known to those skilled in this art.

Further aspects of the subject invention include the genes and isolates identified using the methods and nucleotide sequences disclosed herein. The genes thus identified will encode a toxin active against nematodes or coleopterans. Similarly, the isolates will have activity against these pests.

BRIEF DESCRIPTION OF THE SEQUENCES

SEQ ID NO. 1 is a nucleotide sequence designated V3, useful as a primer according to the subject invention.

SEQ ID NO. 2 is a nucleotide sequence designated V5, useful as a primer according to the subject invention.

SEQ ID NO. 3 is a nucleotide sequence designated V7, useful as a primer according to the subject invention.

SEQ ID NO. 4 is a nucleotide sequence designated ΔV5', useful as a primer according to the subject invention.

SEQ ID NO. 5 is a nucleotide sequence designated ΔV8', useful as a primer according to the subject invention.

SEQ ID NO. 6 is a 16S rRNA forward primer used according to the subject invention.

SEQ ID NO. 7 is a 16S rRNA reverse primer used according to the subject invention.

DETAILED DISCLOSURE OF THE INVENTION

The subject invention concerns nucleotide primers and probes for isolating and identifying *Bacillus thuringiensis* (*B.t.*) genes encoding protein toxins which are active against nematode and/or coleopteran pests. The probes and primers are particularly useful for identification of genes which encode toxins active against corn rootworm. The nucleotide sequences described herein can also be used to identify new *B.t.* isolates having these activities. The invention further concerns the genes, isolates, and toxins identified using the methods and materials disclosed herein.

It is well known that DNA possesses a fundamental property called base complementarity. In nature, DNA ordinarily exists in the form of pairs of anti-parallel strands, the bases on each strand projecting from that strand toward the opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation," of the two strands. If the DNA is then placed in conditions which make hydrogen bonding of the bases thermodynamically favorable, the DNA strands will anneal, or "hybridize," and reform the original double stranded DNA. If carried out under appropriate conditions, this hybridization can be highly specific. That is, only strands with a high degree of base complementarity will be able to form stable double stranded structures. The relationship of the specificity of hybridization to reaction conditions is well known. Thus, hybridization may be used to test whether two pieces of DNA are complementary in their base sequences. It is this hybridization mechanism which facilitates the use of probes of the subject invention to readily detect and characterize DNA sequences of interest.

Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al., 1985). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions and deletions can be produced in a given primer by methods known to an ordinarily skilled artisan. It is important to note that the mutational, insertional, and deletional variants generated from a given primer sequence may be more or less efficient than the original sequences. Notwithstanding such differences in efficiency, these variants are within the scope of the present invention.

In addition, PCR-amplified DNA may serve as a hybridization probe. In order to analyze *B.t.* DNA using the nucleotide sequences of the subject invention as probes, the DNA can first be obtained in its native, double-stranded form. A number of procedures are currently used to isolate DNA and are well known to those skilled in this art.

One approach for the use of the subject invention as probes entails first identifying by Southern blot analysis of a gene bank of the *B.t.* isolate all DNA segments homologous with the disclosed nucleotide sequences. Thus, it is possible, without the aid of biological analysis, to know in advance the probable activity of many new *B.t.* isolates, and of the individual endotoxin gene products expressed by a given *B.t.* isolate. Such a probe analysis provides a rapid method for identifying potentially commercially valuable insecticidal endotoxin genes within the multifarious subspecies of *B.t.*

One hybridization procedure useful according to the subject invention typically includes the initial steps of isolating the DNA sample of interest and purifying it chemically. Either lysed bacteria or total fractionated nucleic acid isolated from bacteria can be used. Cells can be treated using known techniques to liberate their DNA (and/or RNA). The DNA sample can be cut into pieces with an appropriate restriction enzyme. The pieces can be separated by size through electrophoresis in a gel, usually agarose or acrylamide. The pieces of interest can be transferred to an immobilizing membrane in a manner that retains the geometry of the pieces. The membrane can then be dried and prehybridized to equilibrate it for later immersion in a hybridization solution. The manner in which the nucleic acid is affixed to a solid support may vary. This fixing of the DNA for later processing has great value for the use of this technique in field studies, remote from laboratory facilities.

The particular hybridization technique is not essential to the subject invention. As improvements are made in hybridization techniques, they can be readily applied.

As is well known in the art, if the probe molecule and nucleic acid sample hybridize by forming a strong non-covalent bond between the two molecules, it can be reasonably assumed that the probe and sample are essentially identical. The probe's detectable label provides a means for determining in a known manner whether hybridization has occurred.

The nucleotide segments of the subject invention which are used as probes can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{35}S$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. For synthetic probes, it may be most desirable to use enzymes such as polynucleotide kinase or terminal transferase to end-label the DNA for use as probes.

Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probes may be made inherently fluorescent as described in International Application No. WO93/16094. The probe may also be labeled at both ends with different types of labels for ease of separation, as, for example, by using an isotopic label at the end mentioned above and a biotin label at the other end.

The amount of labeled probe which is present in the hybridization solution will vary widely, depending upon the nature of the label, the amount of the labeled probe which can reasonably bind to the filter, and the stringency of the hybridization. Generally, substantial excesses of the probe will be employed to enhance the rate of binding of the probe to the fixed DNA.

Various degrees of stringency of hybridization can be employed. The more severe the conditions, the greater the complementarity that is required for duplex formation. Severity can be controlled by temperature, probe concentration, probe length, ionic strength, time, and the like. Preferably, hybridization is conducted under stringent conditions by techniques well known in the art, as described, for example, in Keller, G. H., M. M. Manak (1987) DNA Probes, Stockton Press, New York, N.Y., pp. 169–170.

Duplex formation and stability depend on substantial complementarity between the two strands of a hybrid, and, as noted above, a certain degree of mismatch can be tolerated. Therefore, the nucleotide sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:

(1) synthesizing chemically or otherwise an artificial sequence which is a mutation, insertion or deletion of the known sequence;

(2) using a nucleotide sequence of the present invention as a probe to obtain via hybridization a new sequence or a mutation, insertion or deletion of the probe sequence; and (3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention.

Thus, mutational, insertional, and deletional variants of the disclosed nucleotide sequences can be readily prepared by methods which are well known to those skilled in the art. These variants can be used in the same manner as the instant probe sequences so long as the variants have substantial sequence homology with the probes. As used herein, substantial sequence homology refers to homology which is sufficient to enable the variant to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | Termination signal | TGA |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A=adenine
G=guanine
C=cytosine
T=thymine
X=T or C is Y is A or G
X=C if Y is C or T
Y=A, G, C or T if X is C
Y=A or G if X is T
W=C or A if Z is A or G
W–C if Z is C or T
Z=A, G, C to T if W is C
Z=A or G if W is A
QR=TC if S is A, G, C or T; alternatively QR=AG if S is T or C
J=A or G
K=T or C
L=A, T, C or G
M=A, C or T The above shows that the amino acid sequence of B.t. toxins can be encoded by equivalent nucleotide sequences encoding the same amino acid sequence of the protein. Accordingly, the subject invention includes probes which would hybridize with various polynucleotide sequences which would all code for a given protein or variations of a given protein. In addition, it has been shown that proteins of identified structure and function may be constructed by changing the amino acid sequence if such changes do not alter the protein secondary structure (Kaiser, E. T., Kezdy, F. J. [1984] *Science* 223:249–255).

The sequences and lengths of five cryV-specific primers useful according to the subject invention are shown in Table 1.

TABLE 1

| Primer name | Sequence | length |
|---|---|---|
| V3 | GATCGTMTWGARTTTRTTCC (SEQ ID NO. 1) | 20-mer |
| V5 | AAAGTNGATGCMTTTATCWGATGA (SEQ ID NO. 2) | 23-mer |
| V7 | ACACGTTATAHDGTTTCTGG (SEQ ID NO. 3) | 20-mer |
| ΔV5' | TCATCWGATAAKGCATCNAC (SEQ ID NO. 4) | 20-mer |

TABLE 1-continued

| Primer name | Sequence | length |
|---|---|---|
| ΔV8' | TGGACGDTCTTCAMKAATTTCYAAA (SEQ ID NO. 5) | 25-mer |

*Bacillus thuringiensis* isolates useful according to the subject invention have been deposited in the permanent collection of the Agricultural Research Service Patent Culture Collection (NRRL), Northern Regional Research Center, 1815 North University Street, Peoria, Ill. 61604, USA. The culture repository numbers of the *B.t.* strains are as follows:

| Culture | Repository No. | Deposit Date |
|---|---|---|
| *Bacillus thuringiensis* PS17 | NRRL B-18243 | July 28, 1987 |
| *Bacillus thuringiensis* PS86Q3 | NRRL B-18765 | February 6, 1991 |
| *Bacillus thuringiensis* PS33F2 | NRRL B-18244 | July 28, 1987 |
| *Bacillus thuringiensis* PS63B | NRRL B-18246 | July 28, 1987 |
| *Bacillus thuringiensis* PS80JJ11 | NRRL B-18679 | July 17, 1990 |
| *Bacillus thuringiensis* PS167P | NRRL B-18681 | July 17, 1990 |

Cultures were deposited under conditions that assure that access to the cultures is available during the pendency of this patent application to one determined by the Commissioner of Patents and Trademarks to be entitled thereto under 37 CFR 1.14 and 35 U.S.C. 122. The deposits will be available as required by foreign patent laws in countries wherein counterparts of the subject application, or its progeny, are filed. However, it should be understood that the availability of a deposit does not constitute a license to practice the subject invention in derogation of patent fights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture(s). The depositor acknowledges the duty to replace the deposit(s) should the depository be unable to furnish a sample when requested, due to the condition of a deposit. All restrictions on the availability to the public of the subject culture deposits will be irrevocably removed upon the granting of a patent disclosing them.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing of *B.t.* Isolates Useful According to the Invention

A subculture of *B.t.* isolates, or mutants thereof, can be used to inoculate the following peptone, glucose, salts medium:

| | |
|---|---|
| Bacto Peptone | 7.5 g/l |
| Glucose | 1.0 g/l |
| KH₂PO₄ | 3.4 g/l |
| K₂HPO₄ | 4.35 g/l |
| Salt Solution | 5.0 ml/l |
| CaCl₂ Solution | 5.0 ml/l |
| pH 7.2 | |
| Salts Solution (100 ml) | |
| MgSO₄ · 7H₂O | 2.46 g |
| MnSO₄ · H₂O | 0.04 g |
| ZnSO₄ · 7H₂O | 0.28 g |
| FeSO₄ · 7H₂O | 0.40 g |
| CaCl₂ Solution (100 ml) | |
| CaCl₂ · 2H₂O | 3.66 g |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *B.t.* spores and/or crystals, obtained in the above fermentation, can be isolated by procedures well known in the art. A frequently-used procedure is to subject the harvested fermentation broth to separation techniques, e.g., centrifugation.

EXAMPLE 2

Isolation and Preparation of Cellular DNA for PCR

DNA can be prepared from cells grown on Spizizen's agar, or other minimal agar known to those skilled in the art, for approximately 16 hours. Spizizen's casamino acid agar comprises 23.2 g/l Spizizen's minimal salts [$(NH_4)_2SO_4$, 120 g; $K_2HPO_4$, 840 g; $KH_2PO_4$, 360 g; sodium citrate, 60 g; $MgSO_4 \cdot 7H_2O$, 12 g. Total: 1392 g]; 1.0 g/l vitamin-free casamino acids; 15.0 g/l Difco agar. In preparing the agar, the mixture was autoclaved for 30 minutes, then a sterile, 50% glucose solution can be added to a final concentration of 0.5% (1/100 vol). Once the cells are grown for about 16 hours, an approximately 1 cm² patch of cells can be scraped from the agar into 300 μl of 10 mM Tris-HCl (pH 8.0)-1 mM EDTA. Proteinase K was added to 50 μg/ml and incubated at 55° C. for 15 minutes. Other suitable proteases lacking nuclease activity can be used. The samples were then placed in a boiling water bath for 15 minutes to inactivate the proteinase and denature the DNA. This also precipitates unwanted components. The samples are then centrifuged at 14,000×g in an Eppendorf microfuge at room temperature for 5 minutes to remove cellular debris. The supernatants containing crude DNA were transferred to fresh tubes and frozen at −20° C. until used in PCR reactions.

EXAMPLE 3

PCR Amplification

Conditions for multiplex PCR amplification were:

TABLE 2

| PCR amplification conditions | |
|---|---|
| Reagent | Final reaction concentration |
| Taq buffer | 1x |
| MgCl₂ | 2.0 mM |
| dNTPs | 0.1 mM |
| rRNA primers (forward & reverse) | 0.05 pmol/μl each |
| cryV-specific primers (forward & reverse) | 0.20 pmol/μl each |
| crude total B.t. DNA¹ | 15 μl |

¹Total reaction volume: 49.5 μl.

Samples were preheated to 94° C. for 3 minutes, then quick chilled on ice. 0.5 μl Taq polymerase was added and overlaid with 50 μl light mineral oil. Cycle conditions were: {94° C., 1 minute; 42° C., 2 minutes; 72° C., 3 minutes +5 second/cycle}, repeated for 30 cycles, and held at 4° C. or −20° C. until gel analysis.

Internal positive controls for each PCR reaction in the screen were included: forward and reverse 16S rRNA gene primers, yielding a PCR-amplified fragment of 182 bp corresponding to nucleotide positions 1188 to 1370 in the sequence (Ash, C. et al. [1991] *Lett. Appl. Microbiol.* 13:202–206). This size is smaller than fragments expected from any of the cryV-specific primer pairs. The two rRNA primers were:

TABLE 3

| Internal positive controls | | |
|---|---|---|
| Primer name | Sequence | length |
| rRNAfor | CCGGAGGAAGGTGGGGATG (SEQ ID NO. 6) | 19-mer |
| rRNArev | CGATTACTAGCGATTCC (SEQ ID NO. 7) | 17-mer |

TABLE 4

| PCR amplification of known nematode-active *B.t.* strains | | | | | | |
|---|---|---|---|---|---|---|
| | | Tentative | Expected size (bp) using primer pair | | | |
| Strain | Gene | gene name | V3-ΔV5' | V3-ΔV8' | V7-ΔV8' | V5-ΔV8' |
| PS17 | 17a | cryVAa | 817 | 1379 | 317 | 582 |
| PS17 | 17b | cryVAb | 526 | 1088 | 317 | 582 |
| PS17 | 86Q3c-like | cryVAc | 337 | 899 | 317 | 582 |

TABLE 4-continued

PCR amplification of known nematode-active B.t. strains

| Strain | Gene | Tentative gene name | Expected size (bp) using primer pair | | | |
|---|---|---|---|---|---|---|
| | | | V3-ΔV5' | V3-ΔV8' | V7-ΔV8' | V5-ΔV8' |
| PS86Q3 | 86Q3a | cryVD | 562 | 1124 | 317 | 582 |
| PS86Q3 | 86Q3c | cryVAc | 337 | 899 | 317 | 582 |
| PS33F2 | 33F2 | cryVB | 547 | 1112 | 320 | 585 |
| PS63B | 63B | cryVC | — | — | — | — |
| PS80JJ1 | 80JJ1 | cryVE | 289 | 860 | 323 | 591 |
| PS167P | 167P (tentative) | TBD | 196 | 800 | 332 | 599 |

EXAMPLE 4

Cloning of Novel Nematode- or Coleopteran-Active Genes Using Oligonucleotide Primers The nematicidal, coleopteran, or specifically corn rootworm-active toxin genes of new *B.t.* strains can be obtained from their DNA by performing the standard polymerase chain reaction procedure as in Example 3 using the oligonucleotides of SEQ ID NO. 4 or SEQ ID NO. 5 as reverse primers and SEQ ID NO. 1, SEQ ID NO. 2, or SEQ ID NO. 3 as forward primers. The expected PCR fragments are approximately 200 to 1000 bp with reverse primer SEQ ID NO. 4 and forward primer SEQ ID NO. 1. Fragments of about 300 to about 1500 bp are expected using the reverse primer SEQ ID NO. 5 and the forward primer SEQ ID NO. 1. The expected PCR fragments are approximately 400 to 800 bp using SEQ ID NO. 5 as reverse a primer, with SEQ ID NO. 2 as a forward primer. Fragments of approximately 200 to 650 bp are expected using the reverse primer SEQ ID NO. 5 and the forward primer SEQ ID NO. 3. Amplified DNA fragments of the indicated sizes can be radiolabeled and used as probes to clone the entire endotoxin gene.

EXAMPLE 5

Screening of *B.t.* Isolates for Genes Encoding Nematode- and Coleopteran-Active Toxins One hundred forty-seven *B.t.* strains were screened by PCR as described in Example 3. Eleven strains were identified as "cryV positive." Approximate sizes of base pair fragments produced from those eleven strains were as follows:

TABLE 5

PCR amplification of DNA from miscellaneous B.t. strains

| Strain | Approximate size (bp) using primer pair | | | |
|---|---|---|---|---|
| | V3-ΔV5' | V3-ΔV8' | V7-ΔV8' | V5-ΔV8' |
| PS54G2 | 470, 530 | 950, 590 | 320 | 585 |
| PS62B1 | 600, 540, 480 | 990, 590, 470 | 320 | 585 |
| PS72N | 560 | 600, 540 | n.d. | n.d. |
| PS74G1 | 530 | 880, 590, 470 | 320 | 585 |
| PS75G2 | 560 | n.d. | 800 | n.d. |
| PS86E | 560 | 600, 540 | n.d. | n.d. |
| PS88F11 | 560 | n.d. | n.d. | n.d. |
| PS98A3 | 530, 390 | 900 | 320 | 585 |
| PS177F1 | 860, 530, 390 | 880, 590, 470 | 320 | 585 |
| PS177G | 530 | n.d. | 320 | 585 |
| PS212 | 620, 530, 470 | 950, 590, 470 | 320 | 585 | n.d. = not determined

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for the systematic identification and isolation of *Bacillus thuringiensis* endotoxin genes encoding toxins against nematodes or coleopterans, wherein said method comprises:

a) amplifying a portion of said gene from total cellular DNA of *Bacillus thuringiensis* by using a primer pair consisting of SEQ ID NO. 3 and SEQ ID NO. 5 wherein said amplification results in the generation of a 317 to 332 nucleotide-long polynucleotide; and b) detecting the presence of said amplification product.

2. A nucleotide palmer pair consisting of SEQ ID NO. 3 and SEQ ID NO. 5.

* * * * *

UNITED STATES PATENT AND TRADEMARK OFFICE
CERTIFICATE OF CORRECTION

PATENT NO. : 5,667,993
DATED : September 16, 1997
INVENTOR(S) : Jerald S. Peitelson, et al.

It is certified that error appears in the above-identified patent and that said Letters Patent is hereby corrected as shown below:

Column 3, line 37: "in the soft." should read --in the soil.--;

line 54: "in the soft." should read --in the soil.--;

line 55: "the soft and" should read --the soil and--.

Column 9, line 62, Table 1: "V5 AAAGTNGATGCMITTATCWGATGA" should read

--V5 AAAGTNGATGCMTTATCWGATGA--

Column 10, line 35: "patent fights" should read --patent rights--

Column 18, line 34, Claim 2: "palmer pair" should read --primer pair--

Signed and Sealed this

Second Day of December, 1997

*Attest:*

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:1:

GATCGTMTWG ARTTTRTTCC                                                        20

( 2 ) INFORMATION FOR SEQ ID NO:2:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

AAAGTNGATG CMTTATCWGA TGA                                              23

( 2 ) INFORMATION FOR SEQ ID NO:3:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

ACACGTTATA HDGTTTCTGG                                                     20

( 2 ) INFORMATION FOR SEQ ID NO:4:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

TCATCWGATA AKGCATCNAC                                                     20

( 2 ) INFORMATION FOR SEQ ID NO:5:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:5:

TGGACGDTCT TCAMKAATTT C Y AAA                                                  25

( 2 ) INFORMATION FOR SEQ ID NO:6:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:6:

CCGGAGGAAG GTGGGGATG                                                            19

( 2 ) INFORMATION FOR SEQ ID NO:7:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:7:

CGATTACTAG CGATTCC                                                              17